US010563012B2

(12) United States Patent
Hegmann et al.

(10) Patent No.: US 10,563,012 B2
(45) Date of Patent: *Feb. 18, 2020

(54) BIODEGRADABLE SIDE CHAIN LIQUID CRYSTAL ELASTOMERS: SMART RESPONSIVE SCAFFOLDS (SRS) FOR TISSUE REGENERATION

(71) Applicant: KENT STATE UNIVERSITY, Kent, OH (US)

(72) Inventors: Elda Hegmann, Kent, OH (US); Torsten Hegmann, Kent, OH (US); Anshul Sharma, Kent, OH (US); Abdollah Neshat, Golestan Province (IR)

(73) Assignee: KENT STATE UNIVERSITY, Kent, OH (US)

( * ) Notice: Subject to any disclaimer, the term of this patent is extended or adjusted under 35 U.S.C. 154(b) by 67 days.

This patent is subject to a terminal disclaimer.

(21) Appl. No.: 15/805,510

(22) Filed: Nov. 7, 2017

(65) Prior Publication Data

US 2018/0105642 A1    Apr. 19, 2018

Related U.S. Application Data

(62) Division of application No. 14/783,892, filed as application No. PCT/US2014/033967 on Oct. 12, 2015, now Pat. No. 9,815,935.

(60) Provisional application No. 61/853,993, filed on Apr. 15, 2013.

(51) Int. Cl.
| | |
|---|---|
| *A61L 27/56* | (2006.01) |
| *C08G 63/91* | (2006.01) |
| *A61L 27/58* | (2006.01) |
| *A61L 27/18* | (2006.01) |
| *C08G 63/08* | (2006.01) |
| *C09K 19/38* | (2006.01) |
| *A61L 31/06* | (2006.01) |

(52) U.S. Cl.
CPC ............ *C08G 63/916* (2013.01); *A61L 27/18* (2013.01); *A61L 27/56* (2013.01); *A61L 27/58* (2013.01); *A61L 31/06* (2013.01); *C08G 63/08* (2013.01); *C09K 19/3866* (2013.01)

(58) Field of Classification Search
CPC ...... A61L 27/18; C08G 63/08; C12N 2537/10
See application file for complete search history.

(56) References Cited

U.S. PATENT DOCUMENTS

| | | | |
|---|---|---|---|
| 5,225,521 A | 7/1993 | Spinu | |
| 5,399,666 A | 3/1995 | Ford | |
| 5,543,218 A | 8/1996 | Bennett et al. | |
| 9,815,935 B2 * | 11/2017 | Hegmann | C08G 63/08 |
| 2003/0105245 A1 * | 6/2003 | Amsden | A61K 47/593 525/450 |
| 2003/0147934 A1 | 8/2003 | Hissink et al. | |
| 2007/0282435 A1 | 12/2007 | Wang et al. | |
| 2009/0299050 A1 | 12/2009 | Zhao | |
| 2010/0323019 A1 | 12/2010 | Lim et al. | |

OTHER PUBLICATIONS

Karikari et al Influence of Peripheral Hydrogen Bonding on the Mechanical Properties of Photo-Cross-Linked Star-Shaped Poly(D, L-lactide) Networks, Biomacromolecules 2005, 6, 2866-2874, Jun. 2005.*
By Xu et al "Synthesis of Amphiphilic Biodegradable Glycocopolymers Based on Poly(e-caprolactone) by Ring-Opening Polymerization and Click Chemistry", Journal of Polymer Science: Part A: Polymer Chemistry, vol. 47, 3583-3594 (2009), published on Oct. 2009.*
E. Fuchs, Stem cells: A new lease on life, Cell 100(1), 143-155 (2000).
X.H. Liu, Nanofibrous hollow microspheres self-assembled from star-shaped polymers as injectable cell carriers for knee repair, Nat. Mater. 10, 398-406 (2011).
S.M. Willerth, Combining stem cells and biomaterial scaffolds for constructing tissues and cell delivery, StemBook, Ed. The Stem Cell Research Community, StemBook, doi/10.3824/stembook.1.1.1 (2008).
N. Jaiswal, Osteogenic differentiation of purified culture-expanded human mesenchymal stem cells in vitro, J. Cell. Biochem. 64, 295-312 (1997).
L.C. Amado, Cardiac repair with intramyocardal injection of allogeneic mesenchymal stem cells after myocardial infarction, Proc. Natl. Acad. Sci. U.S.A. 102, 11474-11479 (2005).
Y. Hong, Collagen-coated polylactide microcarriers/chitosan hydrgel composite: Injectable scaffold for cartilage regeneration, J. Biomed. Mater. Res., Part A 85, 628-637 (2008).
S. Choi, Biodegradable porous beads and their potential application in regenerative medicine, J. Mater. Chem. 22, 11442-11451 (2012).
Y. Senuma, Bioresorbable microspheres by spinning disk atomization as injectable cell carrier: from preparation to invitro evaluation, Biomaterials 21, 1135-1144 (2000).

(Continued)

*Primary Examiner* — Gregory Listvoyb
(74) *Attorney, Agent, or Firm* — Hudak, Shunk & Farine Co. LPA

(57) ABSTRACT

Controlled biodegradable smart responsive scaffold (SRS) materials enhance attachment and viability of cells, i.e. actively guiding their expansion, proliferation and in some cases differentiation, while increasing their biomechanical functionality is an important key issue for tissue regeneration. Chemically build-in functionality in these biodegradable SRS materials is achieved by varying structural functionalization with biocompatible liquid crystal motifs and general polymer composition allowing for regulation and alteration of tensile strength, surface ordering, bioadhesion and biodegradability, bulk liquid crystal phase behavior, porosity, and cell response to external stimuli. Liquid crystal modification of such polymeric scaffolds is an ideal tool to induce macroscopic ordering events through external stimuli. None of these approaches have been demonstrated in prior art, and the use of biocompatible scaffolds that respond to a variety of external stimuli resulting in a macroscopic ordering event is a novel aspect of the present invention.

20 Claims, 12 Drawing Sheets

(56) References Cited

OTHER PUBLICATIONS

H.J. Chung, Highly open porous biodegradable microcarners: invitro cultivation of chondrocytes for injectable delivery, Tissue Eng. A. 14, 607-615 (2008).

C. Perka, Segmental bone repair by tissue-negineered periosteal cell transplants with bioresorbable fleece and bibrin scaffolds in rabbits, Biomaterials 21, 1145-1153 (2000).

E. Hany, Soft biodegradable elastomers based on poly(octanediol-tartarate) for drug delivery and tissue engineering: synthesis characterization and biocompatibility studies, Soft Mater. 9(4), 409-428 (2011).

M.P. Hiljanen-Vainio, Properties of epsilon-caprolactone/DL-lactide (epsilon-CL/DL-LA) copolymers with a minor epsilon-CL content, J. Biomed. Mater. Res. 34, 39-46 (1997).

A.J. Nijenhuis, Crosslinked poly(L-lactide) and poly(epsilon-caprolactone), Polymer 37, 2783-2791 (1996).

H.M. Younes, Synthesis, characterization and in vitro degradation of a biodegradable elastomer, Biomaterials 25, 5261-5269 (2004).

R.F. Storey, Methacrylate-encapped poly(d,l-lactide-co-trimethylene carbonate) oligomers. Network formation by thermal free-radical curing, Polymer 38, 6295-6301 (1997).

M. Lang, Synthesis and structural analysis of functionalized poly(-caprolactone)-based three-arm star polymers, J. Polym. Sci. Part A: Polym. Chem. 40, 1127-1141 (2002).

B. Nottelet, Fully biodegradable polymeric micelles based on hydrophobic- and hydrophilic-functionalized poly (lactide) block copolymers, J. Polym. Sci. Part A: Polym. Chem. 48, 3244-3254 (2010).

N.A. Lockwood, Thermotropic liquid crystals as substrates for imaging the reorganization of matrigel by human embryonic stem cells, Adv. Funct. Mater 16, 618-624 (2006).

A.M. Lowe, Liquid crystalline materials for biological applications, Chem. Mater. 24, 746-758 (2012).

R. Riva, Synthesis of new substituted lactones by "click" chemistry, Archivoc 292-306 (2007).

H.C. Kolb, Click chemistry: diverse chemical function from a few good reactions, Angew. Chem. Int. Ed. 40, 2004-2021 (2001).

H. Nandivada, Fabrication of synthetic polymer coatings and their use in feeder-free culture of human embryonic stem cells, Nat. Protoc. 6, 1037-1043 (2011).

M.A. Matos, Alternating electric field affects on neural stem cell viability and differentiation, Biotechnol. Prog. 26(3), 664-670 (2010).

D.L. Thomsen III, Liquid crystal elastomers with mechanical properties of a muscle, Macromolecules 34, 5868-5875 (2001).

C.F. Soon, Characterization and biocompatibility study of nematic and cholesteryl liquid crystals, Proc. World Congress Engineering, vol. II., ISBN:978-988-18210-1-0 (2009).

N.A. Lockwood, Characterization of the interactions between synthetic LCs and model cell membranes, Liq. Cryst. 34, 1387-1396 (2007).

K.V. Axenov, Thermotropic ionic liquid crystals, Materials 4, 206-259 (2011).

* cited by examiner

BIODEGRADABLE SIDE CHAIN LIQUID CRYSTAL ELASTOMERS: SMART RESPONSIVE SCAFFOLDS (SRS) FOR TISSUE REGENERATION

FIELD OF THE INVENTION

The present invention relates to biomedical engineering, scaffolds, biodegradable polymers, tissue engineering, liquid crystals for biomedical/biological applications, functional lactones, and cell proliferation.

BACKGROUND OF THE INVENTION

Stem cells are known to have a remarkable potential to develop into many different cell types in the body during early life and growth.[1] They also serve as internal repair systems for some tissues to replenish other cells as long as the organ-carrier (humans, animals) is still alive. The combination of stem cells with polymeric scaffolds is a promising strategy for engineering tissues and cellular delivery.[2] Several types of scaffolds have been used in combination with stem cells for tissue engineering applications. Such scaffold materials can generally be classified as natural or synthetic and each have distinct advantages and drawbacks.[3] Several natural or biocompatible synthetic materials have been developed for specific scaffold applications, and many are based on proteins (fibrin, silk), polysaccharides (agarose, alginate), polymers (e.g., PEG), peptides, or ceramic materials. Depending on their chemical nature these types of scaffolds have been studied for bone, cartilage, heart, nerve, retinal and vasculature tissue applications, and can involve directed differentiation of stem cells into mature phenotypes or using the biomaterial scaffolds for expansion of undifferentiated stem cells. None of these approaches, however, has yet demonstrated the use of biocompatible scaffolds that can, by choice, respond to a variety of external stimuli such as temperature, applied fields (electric, magnetic), surface alignment, or mechanic deformation (stress/strain) with a macroscopic ordering event (an increase in order), i.e. a smart responsive scaffold (or SRS).

The advantages of using cell delivery for therapeutic applications are without doubt of significant relevance; it is however the administration methods that are an important key for the success of the treatments sought, such as injecting dispersion of cells directly into injured sites.[4] Other approaches were to encapsulate cells in polymer matrices. Hydrogels were thought to be attractive due to their potential in maintaining cell viability; however they do not offer the necessary mechanical support.[5] Alternative approaches have focused on the use of porous beads for the purpose of cell delivery. Here, beads are cell-loaded and cultured in medium prior to being placed or injected directly into the affected or diseased site.[6] While beads and hydrogels can also contain bioactive agents (growth factors, proteins) they do not guide cells to differentiation into a particular cell lineage. Extreme care should be taken in the choice of cells to be implanted. In this respect, it is of paramount importance to ensure that cells will differentiate into the desirable lineage by 'copying' surrounding cells. If there is heterogeneity of cells at the sites sought for repair, it will ultimately be difficult to predict that cells will respond as desired. Some scaffolds made of natural polymers (fibrin or collagen) have been proven difficult in the area of tissue regeneration because of the necrosis (cell death) found at the center of these scaffold.[7] In addition, these scaffolds presented diminished mechanical properties and instability.

Elastomers, however, have gained considerable attention because they offer many advantages over tough rigid polymers. Most importantly, the physical properties of elastomers can be tuned in a way that they can withstand mechanical tasks such as strain, stress, and impacts because they are soft and deformable.[8] They have also been found suitable as carriers for drug delivery applications. Biodegradable elastomers have been mainly made of two types; thermoplastics[9] and thermosets.[10,11] Thermoplastics are easily made; however, they degrade heterogeneously because of the presence of crystalline and amorphous regions within the material leading to a rapid loss of mechanical strength. While thermosets are not as easily prepared, they do offer more uniform biodegradation rates, better mechanical properties, and chemical resistance. Hence, thermoset elastomers based on three-arm star block co-polymers (SBCs)[10,12] using ring opening polymerization of the suitable monomers followed by cross-linking to form an elastomer are the materials of choice for the preparation of SRS materials.

SUMMARY OF THE INVENTION

The synthesis relates to the use of highly functional liquid crystal elastomers for SRS materials based on star block copolymers (SBCs) with polyols containing from 2 to 8 hydroxyl groups such as glycerol as the central node, from which arms of random blocks of halide substituted caprolactone-, caprolactone- and (D,L)-lactide-based polyester units extent. These elastomers respond to external stimuli such as temperature, elastic deformation (stress, strain) and applied electric and magnetic fields with an increase in ordering. Combined with synthetic structural variations altering hydrophilicity, chirality, tensile strength, biodegradation rate, and cell bioadhesion, such SRS materials (also in form of polymer-multilayer materials) form the basis for controlled and on-demand stem cell mechanobiology. This includes the promotion of cell adhesion over extracellular matrix regeneration and implantation for regeneration of multiple tissues. An easily adjustable, modular design of such SRS liquid crystal elastomers enables easy extension to smart scaffolds for drug delivery via patches on skin, on internal tissue or tumors, for medical implants, general in vitro or in vivo tissue engineering, and for on-demand treatment of neurological, skin, tissue, organ and bone disorders. This approach integrates state-of-the-art soft matter materials synthesis and characterization with stem cell manipulation and multi-modal as well as non-linear optical microscopy for cell optical monitoring.

A star block copolymer having pendant liquid crystal side chains, comprising: a core derived from a polyol; and a plurality of random block polymers comprising: a polymer block derived from halide substituted lactone monomers; a polymer block derived from lactone monomers or isomers thereof; and a polymer block derived from lactide monomers; said halide containing block polymer having a plurality of non-toxic, biocompatible nematic liquid crystal chains pendant therefrom that are substituted for or added at said halide site.

DETAILED DESCRIPTION OF THE OF INVENTION

Figure 1:
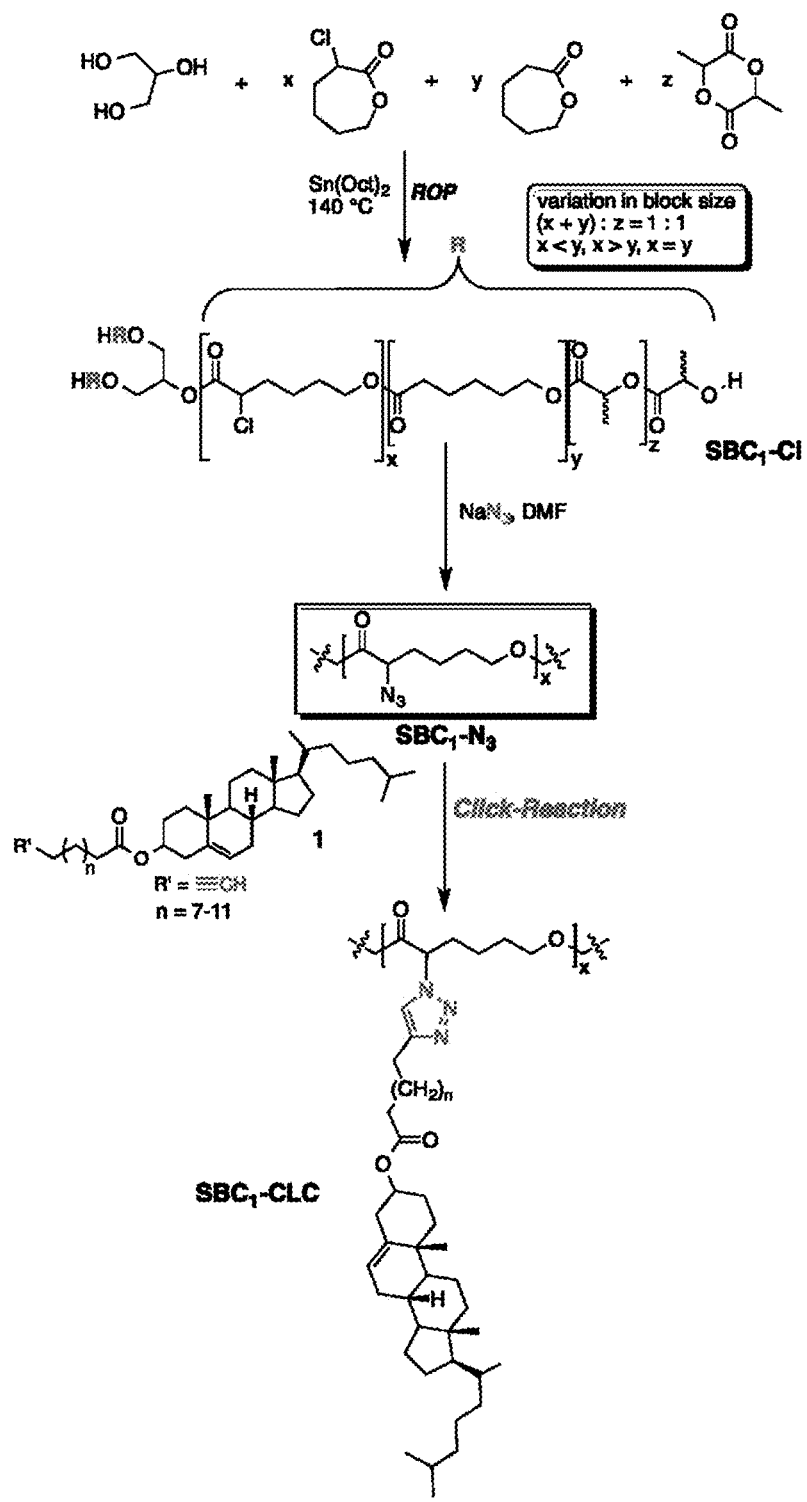
FIG. 1 relates to a synthetic pathway to star block copolymers (SBCs) used for the preparation of SRS materials with biocompatible cholesterol liquid crystal pendants (ROP . . . ring opening polymerization).

The star block copolymers of the present invention are made by the reaction of core polyols with ring opening compounds. The core polyols can have a total of from 2 to about 8, desirably from about 3 to about 6, and preferably 3 or 4 hydroxyl groups with specific examples including glycerol, 2,2-bis(hydroxymethyl)1,3 propanediol, i.e. pentaerythritol:

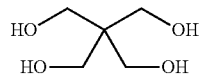

and 2-[[3-hydroxy-2,2-bis(hydroxymethyl)propoxy] methyl]-2-(hydroxymethyl)1,3-propanediol, i.e. dipentaerythritol:

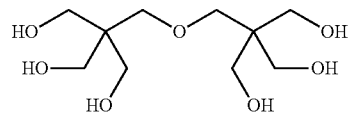 [SMILES: OCC(CO)(CO)COCC(CO)(CO)CO]

Glycerol is generally preferred.

The ring opening compounds generally comprise three different types of compounds. The first types are substituted lactones such as α or γ halide substituted ε-caprolactone wherein in FIG. 1, the substituted group is a chlorine atom and in FIG. 2, the substituted halide is a bromine atom. In FIGS. 1, 2, 3, 10, and 12, the repeat unit drive from the halide substituted ε-caprolactone is denoted by the letter "x".

Another ring opening compound utilized in the present invention is non-substituted lactones such as ε-caprolactone or similar compounds such as its isomers alpha, beta, gamma, and delta caprolactones. Preferred is ε-caprolactone. In FIGS. 1, 2, 3, 10, and 12, the repeat units derive from ε-caprolactone and the like is denoted by the letter "y" in the formulation of the star block copolymer.

A third ring opening polymerization compound that is utilized to form the star block copolymers of the present invention are one or more lactide-based polyesters such as that noted in FIGS. 1, 2, 3, 10, and 12, by the letter "z". The various types of lactides that can be utilized are known to the literature and to the art and are derived from lactic acid $CH_3$—CH(OH)—C(O)OH. Examples of such compounds include D-lactide and L-lactide, with D,L-lactide being preferred.

The star block copolymers of the present invention can have different hydrophobicity that is controlled by initial ratio of the blocks, e.g. x+y/z wherein the two ε-caprolactone-based moieties (blocks x and y) are slightly more hydrophobic than the (D,L)-lactide segment (block z). The molar mass ratio of the x block to the y block is generally from about 0.1% to about 99%, and desirably from about 5% to about 70% and is often close to unity, i.e. about 40% to about 60% based upon the total molar mass of the "x" blocks and the "y" blocks. The molar mass ratio of x+y/z is generally from about 1% to about 90%, and desirably from about 2% to about 80%, and preferably from about 5% to about 40% based upon the total molar mass of the "x", "y", and "z" blocks. The molar mass ratio of x+y to the molar mass of the final elastomer can generally range from about 2% to about 99%, more generally from about 3% to about 80%, and preferably from about 5% to about 40%. The molar mass ratio of x+y can be at least about 5, or 10, or 20, or 30, or at least about 40% of the total mass ratio of the final elastomer. The amount of said core polyol is from about 0.001 to about 50, desirably from about 0.01 to about 40, and preferably from about 0.1 to about 30 mass moles based upon the total of said "x", said "y", and said "z" mass moles. With respect to FIGS. 1, 2, 3, 10, and 12, while the pendant "HRO" groups are not set forth in detail for purposes of brevity, "R", is the star block copolymers as noted in each figure but wherein the number of repeat units of x, y, and z can independently be the same or independently different. Moreover, the order thereof outward from the initiating core polyol can also vary. Thus, it should be appreciated that numerous types of random star block copolymers are encompassed by the present invention.

The reaction of the core polyols with the x, y, and z compounds are known to the art and to the literature. For example, glycerol can be mixed with the ε-caprolactone and the halide substituted ε-caprolactone in any conventional manner such as in a vortex mixer for a short period of time and then the lactide-based polyester can be added thereto. These three compounds are then mixed and then the container can be flushed with nitrogen and placed in an oven until the lactide is completely melted. A tin catalyst such as tin(II) 2-ethylhexanoate is then added and mixed. The container can once again be flushed with nitrogen. The resulting star block copolymer liquid can then be recovered by dissolving it in dichloromethane and precipitating in a methanol dry ice bath.

Once the star block copolymer has been synthesized, it is reacted with suitable compounds that generally replace the halide atom of the lactone compound. Suitable substitution of the halide atoms can be achieved by reacting the pendant halide atom of the "x" block with various metal azide compounds such as $NaN_3$ in suitable solvents such as DMF. For example, sodium azide can be reacted by reaction routes known to the art and to the literature such as lead azide, silver and barium azides (which are shock sensitive detonators or rocket propellants), alkyl or aryl acyl azides or halide azides such as chlorine, bromine and iodine azides or organic azides.

The Azide-Alkyne Huisgen Cycloaddition (or click reactions) reaction is a 1,3-dipolar cycloaddition that occurs between an azide and a terminal (in some other cases an internal) alkyne to give a 1,2,3-triazole (a five member ring). This reaction is best performed in the presence of a copper (I) catalyst. A Ruthenium catalyst is also widely used, and silver (I). The reaction conditions are as follows, the halide substituted star block copolymer is dissolved in dimethylformamide (DMF), sodium azide is added to the solution and allowed to react overnight at room temperature in the presence of any of the catalysts mentioned above (mainly copper (I) iodide). Reaction can also be carried at 35, 40, or 45° C. After that time DMF is removed, mixture is dissolved in toluene, the solution is centrifuged to remove the salt formed (dissolved in toluene). The evaporating toluene to recover the purified product of click reaction.

Such reaction schemes are set forth in FIGS. 1, 2, 3, 10, and 12. An alternate esterification route utilizes an unsaturated carboxylic acid such as butenoic acid where via an atom transfer radical addition (ATRA) the pendant chlorine group of the "x" block copolymer is added to the unsaturated acid. This can be achieved by ATRA that is a reaction technique for the formation of carbon-carbon bonds in the presence of alkyl halides and alkenes. The reaction is typically catalyzed by transition metal complexes of mainly copper and ruthenium. If using diazo initiators such as AIBN, ascorbic or V-70 the amount of metal catalysts.

Pendant liquid crystals are utilized to impart a smart responsive property to the star block copolymers of the present invention. The choice of liquid crystal pendants suitable for the functionalization of the star block copolymers used for SRS substrates is naturally limited to non-toxic, biocompatible liquid crystalline compounds. In spite of these stringent requirements, classes of liquid crystals are known to be non-toxic and biocompatible, such as cholesterol-based chiral nematic[21] liquid crystals or any derivative thereof, or any cholesteryl liquid crystal or derivative thereof such as cholesteryl-5-hexynoate, or the sufonated cholesteryl liquid crystal of FIG. 11, or any 3,4-difluorophenyl-bicyclohexyl-based nematic liquid crystals or any derivative thereof, see FIG. 11, bottom (closely related to the structurally identical nematic mixture TL205 used by Abbott et Examples of such suitable nematic cholesterol liquid crystals include the liquid crystals set forth in FIG. 1, the two liquid crystals set forth in the bottom of FIG. 11, as well as the two liquid crystals set forth in the bottom of FIG. 12 wherein "n" is from about 5 to about 30, or from about 7 to about 11. The synthesis of the cholesterol liquid crystal pendant starts from commercially available cholesterol, which is alkylated with 1,ψ-dihydroxyalkanes or 1,ψ-alkynols to give chiral nematic cholesteryl derivatives that can be incorporated into the SBCs. This can be accomplished either by esterification via a preceding atom transfer radical addition (ATRA) of 3-butenoic acid to the -chloro-caprolactone units, or by a Cu-catalyzed Huisgen 1,3-dipolar cycloaddition ("click" reaction)[24] after displacement of the chloro with an azide group next to the carbonyl group (see FIG. 12).

Generally, any cholesterol related compound can be used as pendant groups that have been modified to contain other types of reactive groups as for example an ionic sulfonate group.[25]

EXAMPLES

Synthesis of Monomers and Preparation of Elastomers

Figure 2:
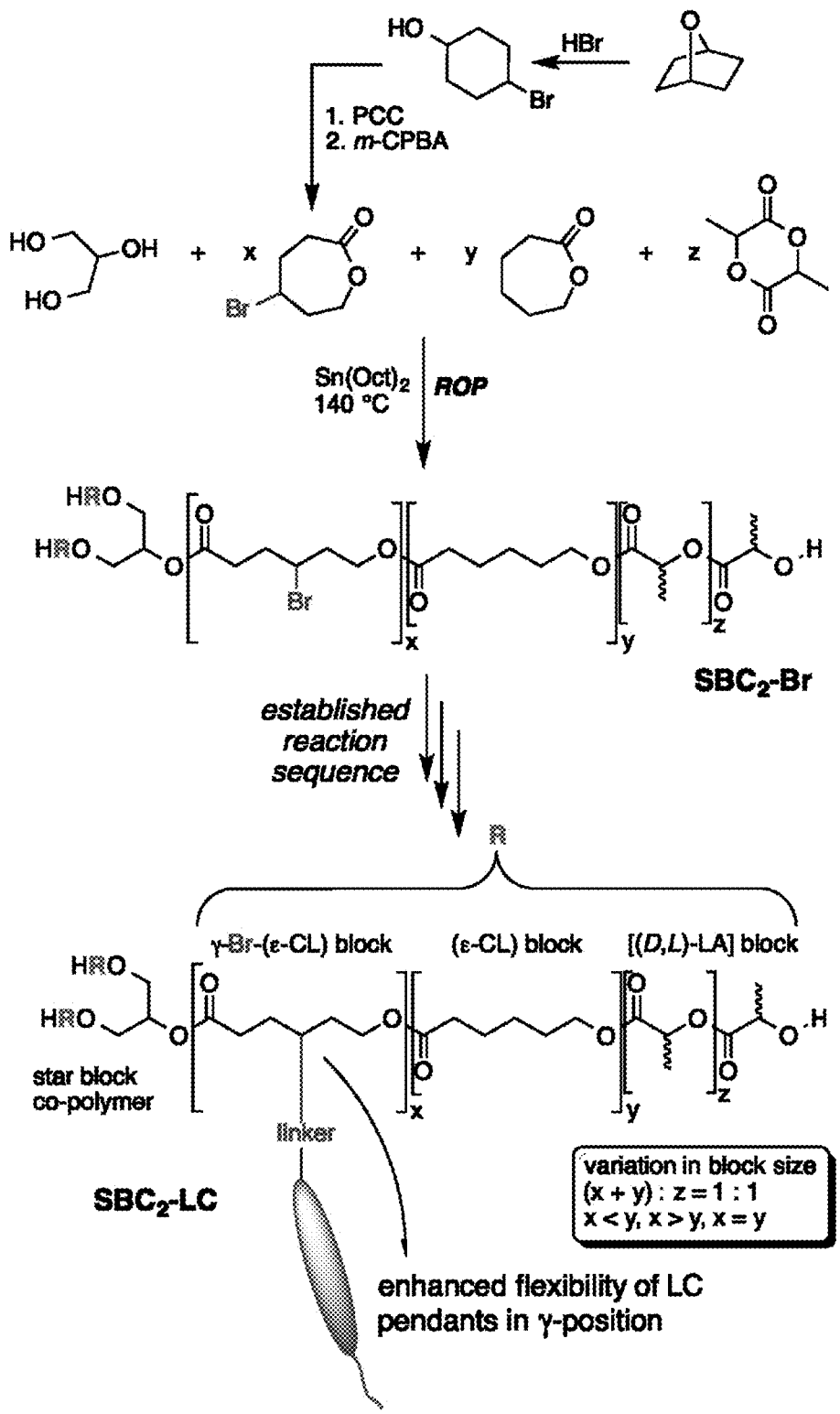
FIG. 2 relates to synthesis of star block copolymers with enhanced flexibility of the liquid crystal pendants provided by functionalization of ε-caprolactone in the γ-position (farther away from the neighboring C═O, hence, the branching points).
Figure 3:
FIG. 3 relates to a simplified structure of poly(ε-caprolactone)-co-(D,L)-lactide liquid crystal elastomers used as SRS materials (bottom) obtained from star block copolymers (SBCs) with various liquid crystal pendant groups.

The synthesis of highly functional liquid crystal elastomers for SRS materials is based on star block copolymers (SBCs) with a glycerol central node, from which arms of random blocks of ε-caprolactone-, α- or γ-substituted ε-caprolactone- and (D,L)-lactide-based polyester units extent (FIGS. 1 and 2).

α-Cl-ε-CL is prepared following a procedure developed by Jerome et al.[14] Briefly, 2-chlorocyclohexanone (10 g, 75.0 mmol) was dissolved in dry dichloromethane (15 mL). The oxidizing agent, meta-chloroperbenzoic acid (m-CPBA) (20 g, 115 mmol), was dissolved in dry dichloromethane (15 mL) and it was added to the 2-chlorocyclohexanone solution. The reaction mixture was stirred under nitrogen for four days. The meta-chlorobenzoic acid (m-CBA) byproduct was precipitated by cooling the reaction mixture at −20° C. for 1 hour. The byproduct was filtered and the remaining solution was washed with saturated solutions of sodium sulfate, sodium bicarbonate, and sodium chloride. Then, the solvent was removed under reduced pressure and the pale yellow viscous liquid was purified by distillation under reduced pressure. The main fraction collected by distillation under reduced pressure at 0.1 mmHg and at a temperature of 90° C.

γ-Br-ε-CL is prepared following a procedure developed by Jerome et al.[16] 4-bromocyclohexanone (1.56 g, 8 mmol), obtained by the oxidation of 4-bromocyclohexanol with pyridinium chlorochromate (PCC), was dissolved in dichloromethane (20.0 mL). To this solution, m-CPBA (1.52 g, 8.8 mmol) was added and the mixture was stirred at room temperature for 24 h. The m-CBA byproduct was precipitated by cooling the reaction mixture to −20° C. for 1 hour. The byproduct was filtered and the remaining solution was washed with saturated solution of sodium thiosulfate and sodium bicarbonate. Then, the organic phase was dried with sodium sulfate and the solvent was evaporated under reduced pressure, leaving light yellow oil as product.

Synthesis of star-poly(ε-CL-co-α-Cl-ε-CL-co-DL-LA), ($SBC_1$-Cl).

The general procedure for the synthesis of star copolymer (SCP) of ε-CL and DL-LA, developed by Amsden et al.,[13] was followed and slightly modified as follows: In a dry, silanized ampoule, glycerol (2.48 μl, 0.034 mmol) was mixed with ε-CL (3.62 g, 31.7 mmol) and α-Cl-ε-CL (0.5 g, 3.3 mmol) and mixed using a vortex mixer or about a minute, then, D,L-LA (7.21 g, 33.9 mmol) was added. The solution was mixed again using the vortex mixer, the ampoule was then flushed with nitrogen and placed in the oven at 120° C. until the D,L-LA completely melted. The contents were mixed on a vortex mixer and tin(II) 2-ethylhexanoate (66 µl, 0.202 mmol) was added and mixed one last time. The ampoule was then flushed with nitrogen, flame-sealed under vacuum, and placed in a sand bath for 48 hours at 140° C. The seal was then broken and the highly viscous liquid was dissolved in dichloromethane. The solution was then poured into methanol cooled using a dry ice/acetone bath (at −78° C.). A white precipitate was obtained and was removed by filtration.

Star-poly($\epsilon$-CL-co-$\gamma$-Br-$\epsilon$-CL-co-DL-LA), ($SBC_2$—Br) is prepared following the same procedure for $SBC_1$-Cl with the difference that 2-Br-$\epsilon$-CL was used instead of $\alpha$-Cl-$\epsilon$-CL.

2,2-Bis(1-caprolactone-4-yl) propane (BCP)[17] is prepared in two steps following a procedure developed by Albertsson et al.[17] In general, a flask was charged with 2-bis(4-hydroxycyclohexyl)propane (10.8 g, 45 mmol) and acetic acid (52 mL). Then, $CrO_3$ (11 g, 110 mmol) solution in acetic acid (50 mL) and distilled water (8 mL) was added dropwise over a period of 2 h to the previous flask, while maintaining the mixture temperature at 17 to 20° C. using ice and water bath. After 30 minutes, 2-propanol (50 mL) was added to RB flask. The solution was stirred overnight. After 24 h, the dark purple solution was concentrated under reduced pressure and a light purple solid was precipitated by the addition of distilled water to the flask. The crude product was filtered using a glass frit and the solid material was washed multiple times with distilled water until a white solid material is obtained. Further purification by the crystallization in benzene yielded a solid material with a melting point compatible with the previously reported number in the literature. In the next step, dry diketone (8.34 g, 35 mmol) was dissolved in dry dichloromethane (75 mL) and m-CPBA (6 g, 35 mmol) solution in dry dichloromethane (75 mL) was added to the flask. The mixture was refluxed for 24 h. Then, the m-CBA byproduct was precipitated by cooling the reaction mixture to −78° C. for 10 minutes. The byproduct was filtered and the remaining solution was concentrated under reduced pressure. The viscose crude product was washed with 2-heptanone and the precipitate was dried under reduced pressure at 50° C. overnight.

Synthesis of Cholesteryl 5-hexynoate, 5-hexynoic acid 3 g (26.7 mmol) and 130 mL dry dichloromethane were mixed in a round bottom flask before it was cooled to 0° C. using ice bath, following Donaldson et al. procedure.[18] On another round bottom flask cholesterol (10.3 g, 26.7 mmol), dicyclohexylcarbodiimide (8.28 g, 40 mmol), and 4-dimethylaminopyridine (0.2 g) were mixed. The 5-hexynoic acid solution was transferred stepwise to the flask that contained the cholesterol mixture and the final mixture was maintained at 0° C. for 1 h. Then, it was allowed to warm up to room temperature overnight. The resulting precipitate (dicyclohexylurea byproduct) was removed by filtration and discarded. The filtrate was concentrated under reduced pressure; the collected residue was dissolved in hexane solution. After evaporating hexane under reduced pressure, an excess of ethanol was added to the oily residue to collect the final product. An off-white solid was formed immediately which was washed with ethanol. The solid product was dried under vacuum at 50° C.

Synthesis of star-poly($\epsilon$-CL-co-$\alpha$-cholesteryl 5-hexynoate-$\epsilon$-CL-co-DL-LA), ($SBC_1$-CLC) by Click Reaction In a round bottom flask 1 equivalent of $SBC_1$—$N_3$ (1.5 g, 33 mmol) was dissolved in freshly distilled THF, then 1.2 equivalent of cholesteryl 5-hexynoate (1.94 g, 4.03 mmol), 0.1 molar equivalent of copper iodide (0.06 g, 0.33 mmol), and 0.1 molar equivalent of triethylamine (0.03 g, 0.33 mmol) were added. The mixture stirred overnight at 35° C. under nitrogen. Then, the solvent was evaporated under reduced pressure. The residual mixture was dissolved in dichloromethane and was centrifuged to remove unreacted materials and side products.

Synthesis of star-poly($\epsilon$-CL-co-$\gamma$-cholesteryl 5-hexynoate-$\epsilon$-CL-co-DL-LA), ($SBC_2$-CLC) by Click Reaction In a round-bottom flask $SBC_2$—$N_3$ (1.50 g, 0.700 mmol) was dissolved in 15 mL dry DMF. Then, cholesteryl 5-hexynoate (0.4 g, 0.832 mmol, 1.2 equiv), CuI (0.0132 g, 0.0690 mmol, 0.1 equiv.), and triethylamine (0.07 g/9.68 µL, 0.069 mmol, 0.1 equiv.) were added to the flask. The solution was stirred overnight at 35° C. The reaction progress was monitored by IR spectroscopy after 24 h. The disappearance of the azide band at 2096 $cm^{-1}$ indicated that the reaction was complete. The click reaction product was precipitated in cold methanol, filtered, and dried under reduced pressure.

Synthesis of the $SBC_1$-Elastomer. star-poly($\epsilon$-CL-co-$\alpha$-cholesteryl 5-hexynoate-$\epsilon$-CL-co-DL-LA)

Figure 4:
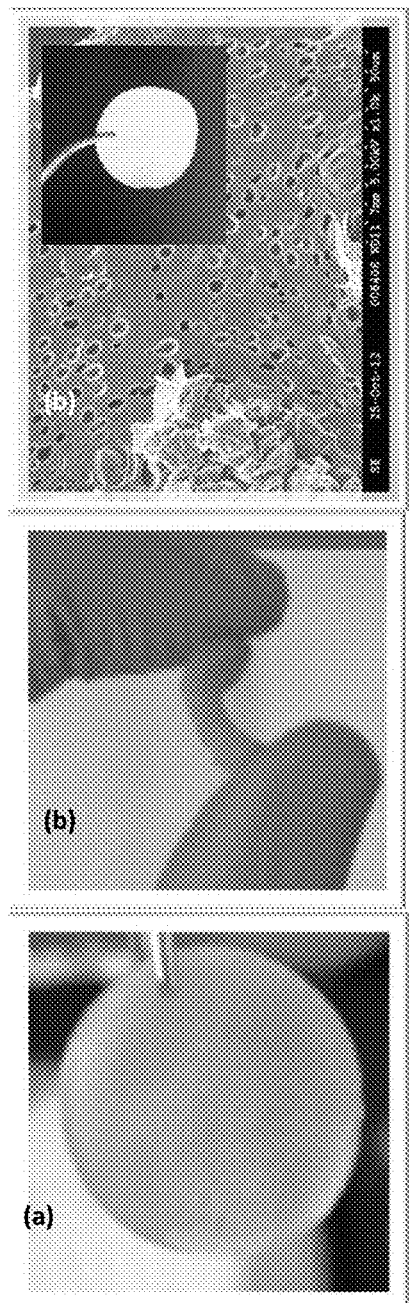
FIG. 4 relates to (a) top view a position (b) and side view g position (c) SEM pictures of 60μ elastomer with liquid crystal moiety in γ position of the caprolactone block elastomer.

Amsden's chemical cross-linking procedure to synthesize elatomer-1 and elastomer-2 was followed. In general, a 3:1 mass ratio of SBC:BCP and also a molar ratio of 2.3:1 for $\epsilon$-CL:BCP were used. In a dry silanized ampule, BCP (1 g) and of $\epsilon$-CL (1 g) were mixed and heated in an oven or a sand bath to 140° C. until the BCP was dissolved. Then, SCP-LC-1 (3 g) was added to the ampoule and the contents were mixed using a vortex mixer. Once the mixture was homogenous, tin(II) 2-ethylhexanoate catalyst (0.0324 mL) was added and the ampoule was then flame-sealed. The closed ampoule was placed in a sand bath at 140° C. for approximately 18 h. The resulting elastomer was removed from the ampoule and washed with 70% ethanol solution to remove unreacted products and prepare for biocompatibility tests dried under vacuum before analysis. The same procedure was followed for $SBC_2$-Elastomer. Elastomer can also in their final state be poured into molds and placed in an oven at 140° C. for approximately 18 h in order to obtain other desired shapes (FIG. 4).

As noted, the smart responsive nature of these SRS materials is made by the use of pendant liquid crystal functional moieties wherein ordering and alignment can be manipulated using various substrates (commonly used for alignment of LC molecules in display devices), applied electric and magnetic fields, or mechanical deformation (stretching, twisting) to manipulate/steer direct differentiation of stem cells, control cell adhesion and growth rate, and potentially allow for simultaneous incorporation of oriented vascular networks, for example, by co-culturing of endothelial cells. In a quasi solvent-less, melt-polymerization at 140° C., which is easily be scaled up to considerable quantities, the hydrophilic-hydrophobic balance critical for cell attachment is easily controlled by the initial ratio of the building blocks (x+y/z), with the two ε-caprolactone-based moieties as hydrophobic and the (D,L)-lactide units as hydrophilic segment.[18]

The degree of liquid crystal functionalization is controlled by the ratio between x and y, and determines both thermal and macroscopic liquid crystalline properties of the SBC and the final liquid crystal elastomer, in addition to the chiral properties when cholesteryl units are used (FIG. 1). Abbott and co-workers demonstrated the interplay between liquid crystal ordering and stem cell attachment and proliferation on Matrigel™-covered liquid crystal-stem cell interfaces,[19] and these experiments described by the Abbott group serve as a guide for the choice of liquid crystal pendant groups described here.

Enhancing the mobility (reducing steric constrains) of the liquid crystal pendant groups in the star block copolymer as well as the final elastomer is also possible by relocating their position on the SBC backbone using γ-bromo-substituted ε-caprolactone as summarized in FIG. 2. In comparison to $SBC_1$ (based on α-chloro-ε-caprolactone) in $SBC_2$ the liquid crystal pendants are attached in the center of the substituted-bromo-caprolactone block. As noted above, it is important that the three blocks (x, y, and z) are randomly distributed throughout the block copolymer arms. This reaction sequence could ultimately also provide more control over the number of liquid crystal pendants in the final elastomer since -bromo-caprolactone could be functionalized with the liquid crystal moiety prior to co-polymerization, a path not accessible for α-chloro-ε-caprolactone.[15]

An important point of the design is the degree of cross-linking in the final liquid crystal elastomer that is controlled by the amount of cross-linker (bis-ε-caprolactone, blue in FIG. 3) added to the SBCs in the final step. Here, the degree of cross-linking is used to tune not only the thermal and mechanical properties of the SRS elastomers, but also the porosity, which will allow for integration (by swelling and soaking up) of collagen and growth factors as described later. The choice of a hydrophilic cross-linker also simplifies the process of cell seeding and nutrient transport in the aqueous cell culture medium, but also allow us to enhance the porosity even further; even manipulate by the addition of ions, given the ethylene glycol (grown ether) nature of the spacer segments (blue cross-linker in FIG. 10).

Figure 10:
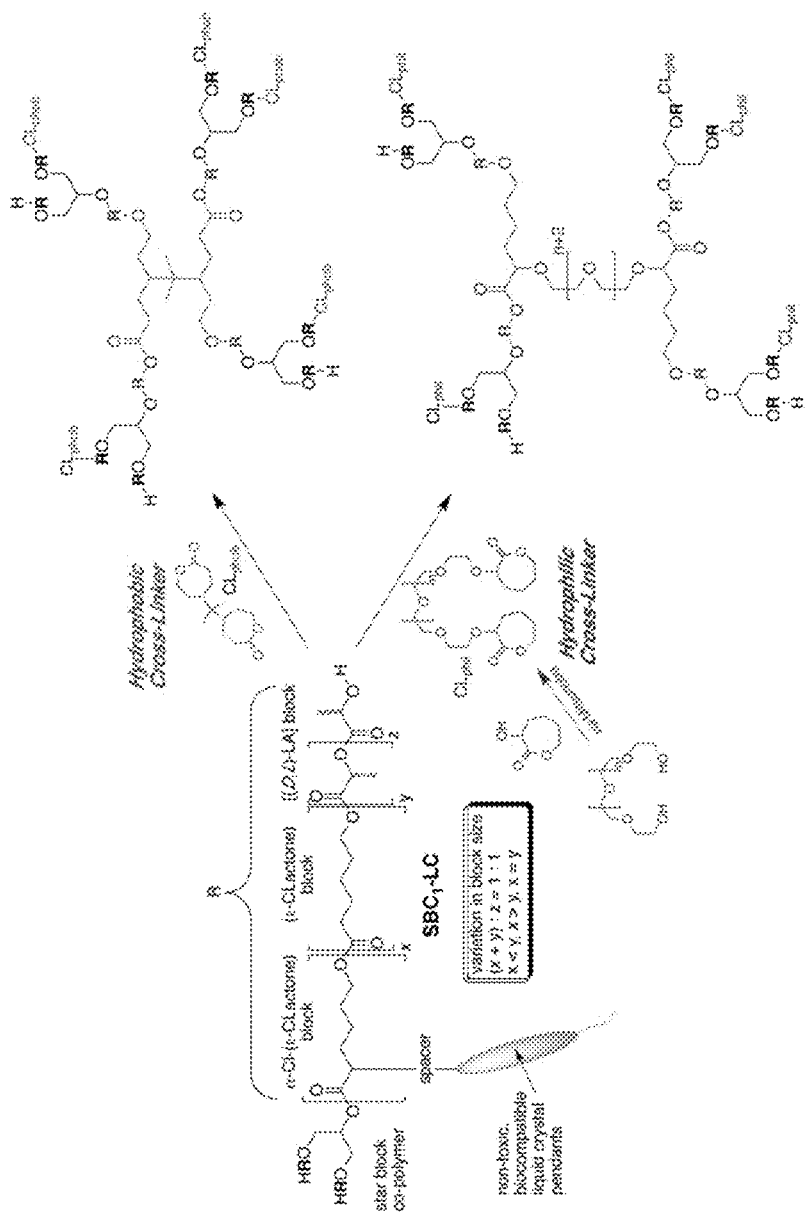
FIG. 10 relates to hydrophobic and hydrophilic cross-linker to synthesize elastomers from the SBCs. The hydrophilic cross-linker is prepared in one step from commercially available α-hydroxy-ε-caprolactone and oligoethyleneglycols differing in length (n=4, 5, 6 . . . any length) via Mitsunobu etherification. The increased spacer length of the hydrophilic cross-linker in comparison to bis-caprolactone (green) leads to larger pore sizes in the elastomer.

Crosslinkers include compounds that are biocompatible and biodegradable with respect to the star block copolymer and include compounds such as 2,2-Bis(1-caprolactone-4-yl) propane (BCP) and derivatives thereof, and Bis-caprolactone with oligoethylene glycol spacer and derivatives thereof, as shown in FIG. 10.

All elastomers retain their structural integrity and biomechanical strength for a period of time enough for cell adherence, growth, and proliferation. Elastomers seeded with cells also maintain their elastic and mechanical properties, are soft and deformable.

In crosslinking elastomers, we followed Amsden's et al. chemical cross-linking procedure using bis-caprolactone (BCP) as crosslinker that is a general Ring Opening polymerization of the BCP. To prepare the elastomer a 3:1 mass ratio of $SBC_xCLC$:BCP and also a molar ratio of 2.3:1 for ε-CL:BCP were used (ε-CL as solvent). In a dry silanized ampoule, BCP and of ε-CL are mixed and heated in a sand bath to 140° C. until the BCP was dissolved. Then, $SBC_x$-CLC was added to the ampoule and the contents were mixed using a vortex mixer. Once the mixture was homogenous, tin(II) 2-ethylhexanoate catalyst is then added. All contents of the ampoule were mixed using vortex and then the ampoule was flame-sealed. The closed ampoule was placed in a sand bath at 140° C. for approximately 18 h. BCP can be substituted by any bis-caprolactone compound. The BCP can be substituted by any bis-caprolactone. Several other crosslinkers can be used, but the need to be biocompatible and biodegradable will eliminate the use of most cross-linkers widely used for the preparation of elastomers. Catalyst, tin(II) 2-ethylhexanoate, can be replaced by TBD, Zinc or Ni-based catalysts, any other metal catalysts (Li, Na, K, Mg, Ca, Sr, Al, Sn, Ti, V, Fe, Be, Zr, Hf, Sc, Y, Nd, Sm, Eu, Gd, Yb, Lu) and enzyme based catalysts. Other methods can include UV crosslinking, howver it will require extra synthetic steps to attach unsaturated moieties prior UV cross-linking.

Synthetically, the ratios determining hydrophilic-hydrophobic balance, degree of liquid crystal functionalization (x+y and x+y/z), and mechanical properties (stiffness, flexibility, porosity) is readily adjusted if cell adhesion to increasingly hydrophobic or too stiff/flexible SRS films is needed. This is relevant if additional Matrigel™ layer needs to be avoided (applied by dipping, drop-casting or spin-coating), in contrast to previous experiments described by Abbott and co-workers,[14a] that could mask the surface ordering of the liquid crystal elastomers to some extent.

This synthetic flexibility permits the construction of SRS materials varying in internal structure and macroscopic properties such as hydrophilicity, chirality, tensile strength, surface properties, biodegradation rate, bioadhesion susceptibility, and bulk liquid crystal phase behavior. An adjustable internal structure provided by different synthetic approaches is a key benefit for tunable porosity. Data show pore sizes ranging from about 10 to about 30 μm determined by scanning electron microscopy, which will increase by swelling the elastomers to about 20 micron to about 60 micron in various buffer solutions or cell culture media-mesenchymal stem cells for example are about 10 to about 20 micron in diameter), thereby enhancing cell-SRS elastomer interactions (i.e. cells can infiltrate the scaffold) and allowing space for extracellular matrix regeneration (ECM). Tunable porosity as well as the hydrophilic-hydrophobic balance allows us to tune the physical properties of the material to adapt to any type of cells candidates for tissue engineering purposes or as 2D or 3D models for research study. A broad range of porosity is from about 5 micron to about 700 micron, medium size porosity is from about 10 micron to about 500 micron and desirable porosity range is from about 10 micron to_about 350 micron in the dry state before immersed in culture media or phosphate buffers.

Figure 5:
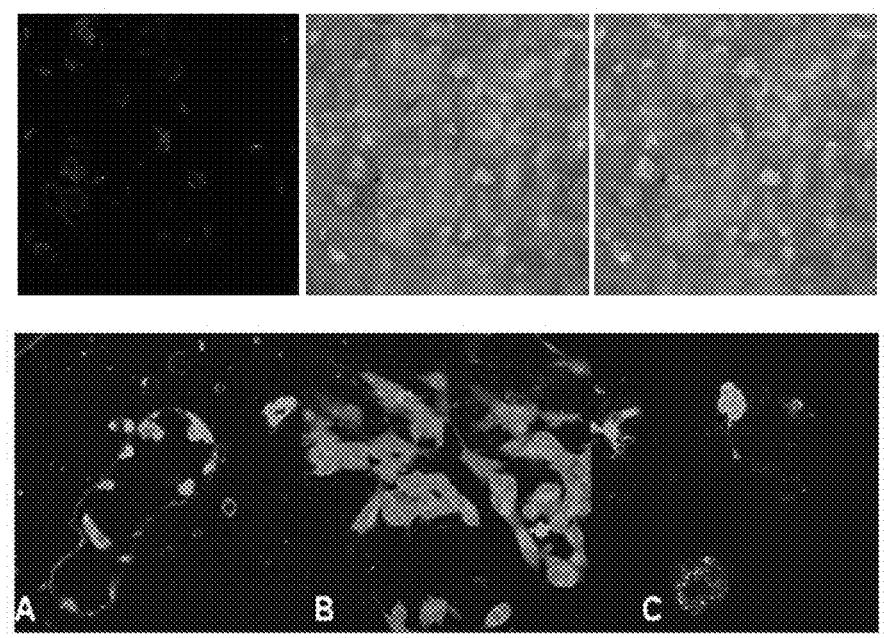
FIG. 5 relates to human neuroblastomas (SH-Sy5Y) grown for seven days on $SBC_2$-LC, top and a) natural state, b) coated with collagen, and c) D-lysine; prior staining with DIOC6 (green) or nuclear stain (blue).
Figure 6:
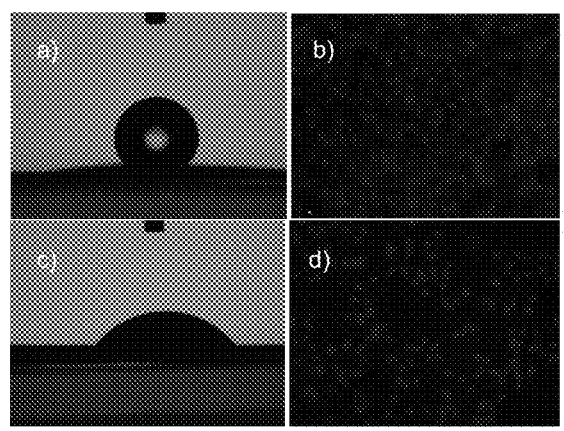
FIG. 6 relates to a) and b) C2C12 Myoblasts seeded onto untreated elastomer for 7 days; total coverage <40%. Coverage areas displayed high cell density. c) and d) C2C12 Myoblasts seeded onto $O_2$ plasma cleaned elastomer for 7 days; total coverage >90%. Homogenous cell density throughout.
Figure 7:
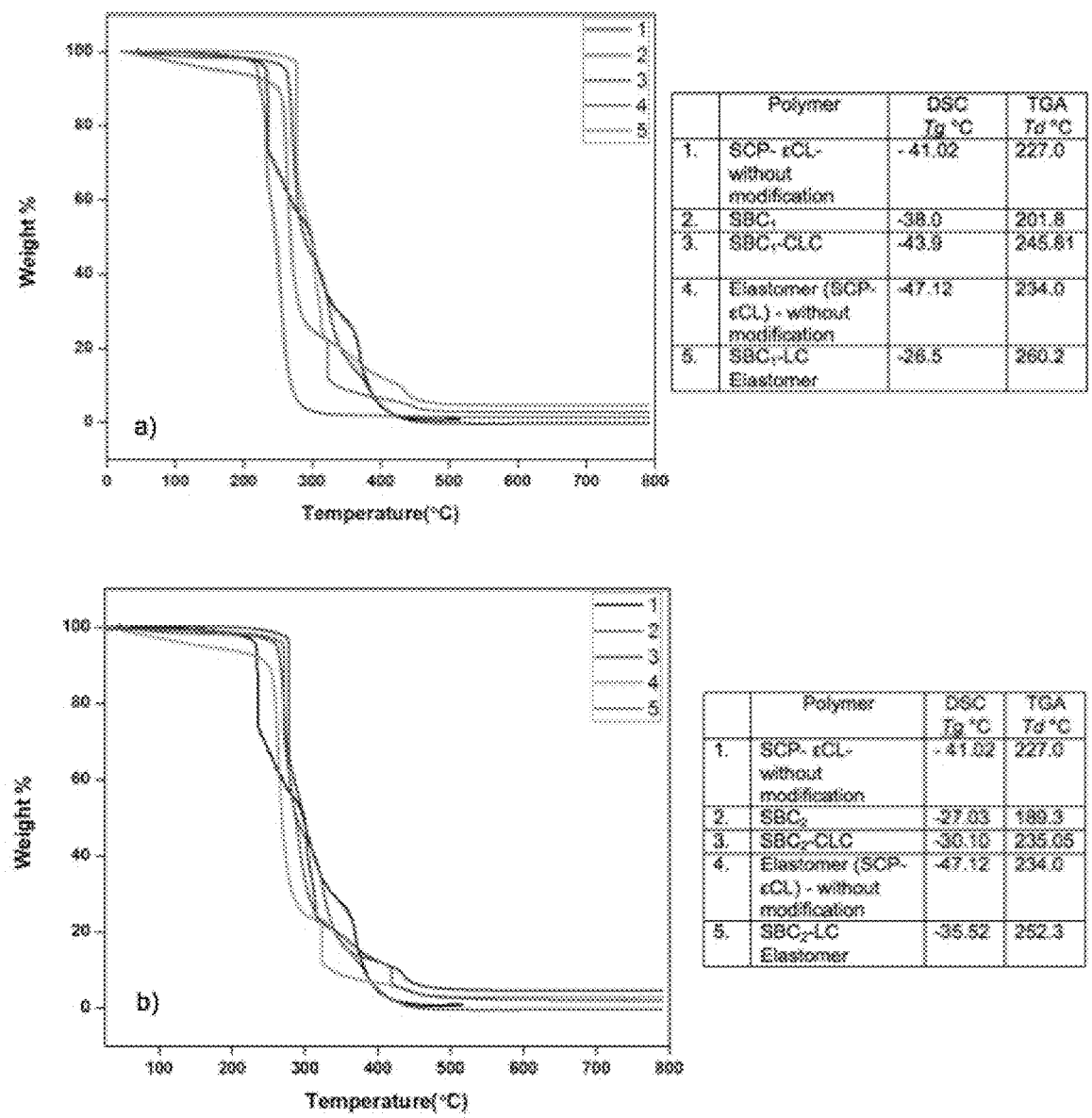
FIG. 7 relates to a) Thermogram and DSC data for $SBC_1$ series and b) Thermogram and DSC data for $SBC_2$ series.

SRS are compatible with cell differentiation, growth and survival of cultured neurones and glia. We have shown that cells are viable when grown on elastomers, can differentiate and survive for extended periods (>1 month) as shown in FIG. 5. FIG. 6 shows the versatility of SRS on other types of cells such as myoblasts, elastomers were exposed to plasma 02 and the hydrophobicity of the material was decreased allowing for an increase in density of myoblasts within the 3D SRS network. SRS are also more stable than the elastomers created by Amsden[10] showing a decomposition temperature above 250° C. and Tg between −26° C. to −50° C., well below physiological temperatures as expected for biodegradable elastomers (FIG. 7).

Figure 8:
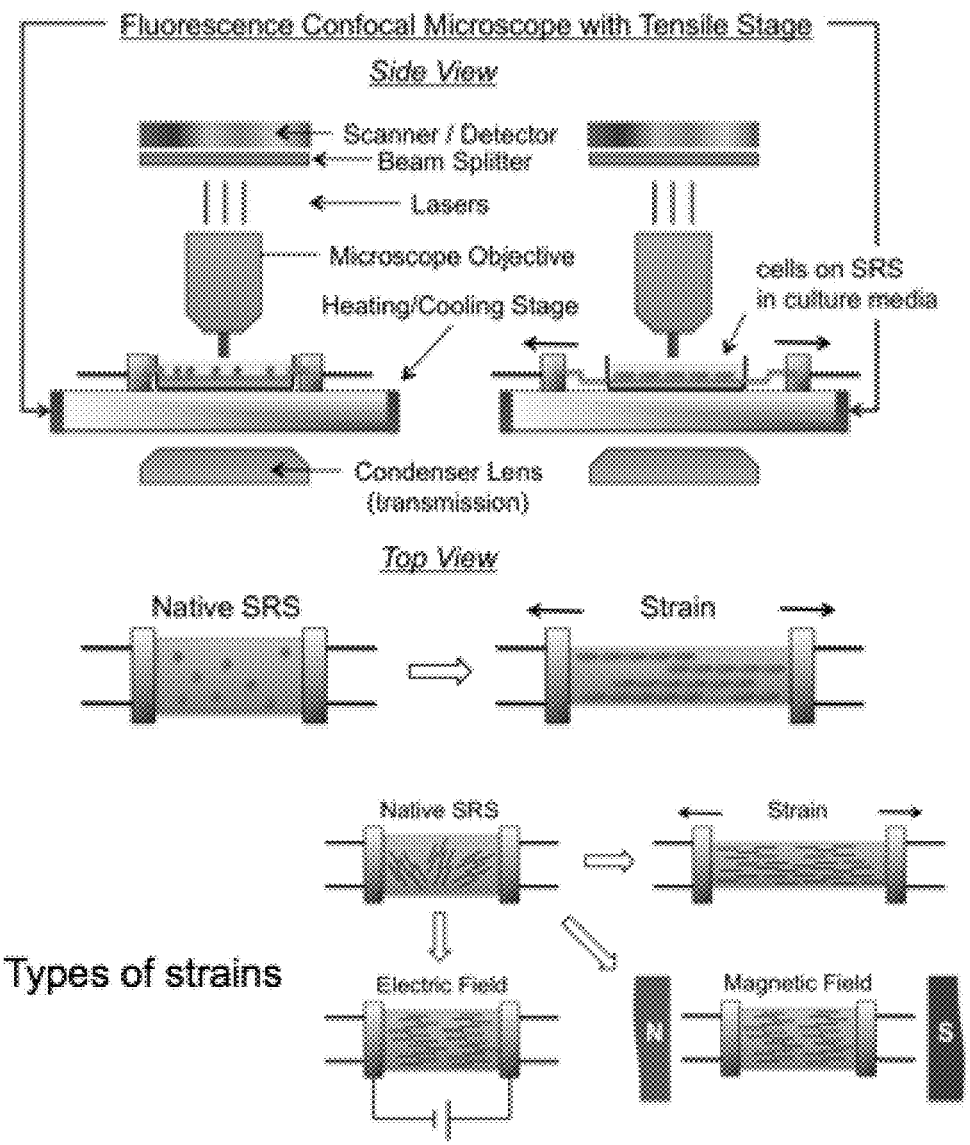
FIG. 8 relates to experimental setup for the observation of mechanically induced stem cell differentiation using a temperature-controlled microscope tensile stage. The bottom images show the expected alignment, expansion and on-demand differentiation of mesenchymal stem cells.
Figure 9:
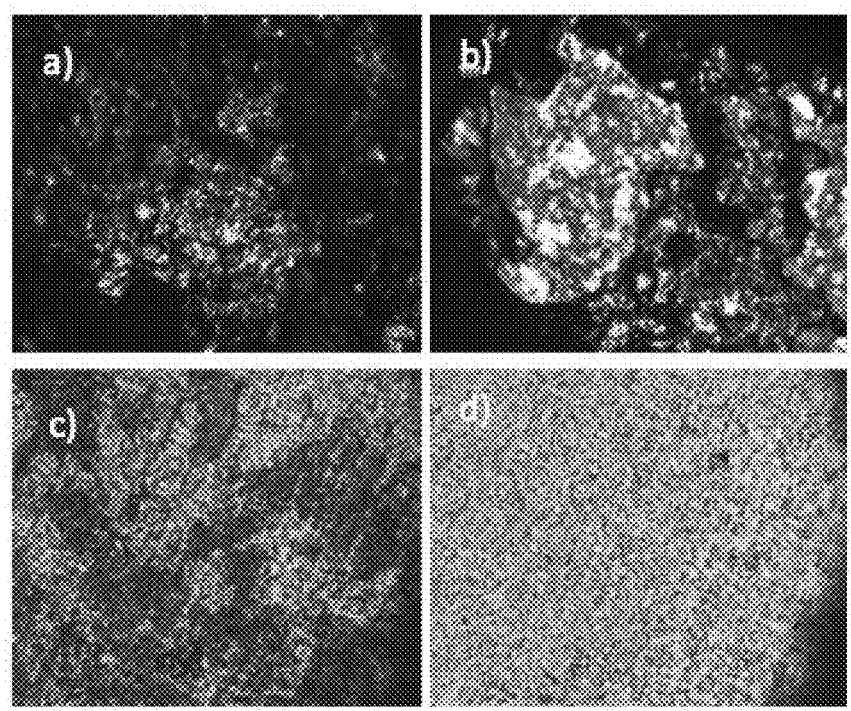
FIG. 9 relates to rheological studies coupled with polarized optical microscopy: Angular displacement for $SBC_2$-LC θ of 45°: at a) 65° C., then b) 74° C. Angular displacement; e of 45°: at c) 50° C., then d) 65° C.

SRS materials can be placed inside a temperature-controlled tensile stage that allows us to apply a constant strain force. This tensile stage interfaced with a polarized light optical microscope permits both bright field and polarized light observation of the liquid crystal elastomer (FIG. 8). This is useful in the case of stem cells seeded on to/within the porous elastomer the stage is programmed to slowly and stepwise increase strain on the elastomer (mildly enough to not irreversibly damage the cell membrane), allowing the surface (topology of the elastomer) as well as the inherent liquid crystalline order to change (increase), and, in turn, forcing alignment of the cells. This procedure is done stepwise allowing the cells to slowly adapt to their new environment triggering on-demand differentiation. The elastomer alignment can be followed using polarized light optical photomicroscopy (as studied in FIG. 9); the cholesteric moiety of the elastomer shows a change in the birefringence (texture), while the cells are monitored in bright field without the polarizers.

This mechanical stimulation of cells grown on SRS films, via mechanical deformation induced ordering of the liquid crystal elastomers, is thought to promote ECM formation and improve the cells' biomechanical functionality. It has been established that scaffolds need to be synthesized in a way that provides physical stimuli to cells. Physical stimuli of cells in turn will play a key role in the regeneration of tissue and organ adequate functions.

The use of molds and extrusion methods is possible and the design of 2D multi-layer liquid crystal-based SRS materials for stem cell mechanobiology is anticipated using these liquid crystal elastomers and other commercially-available, synthetic biocompatible polymers such as poly(isopropyl acrylate) (PIPA)—a temperature-responsive polymer—as sub-layers.[22]

Taking advantage of the liquid crystalline properties of the SRS materials, three additional stimulus pathways to trigger stem cell differentiation are realistic. Either alone or in combination with the tensile strain described already, magnetic or electric fields (FIG. 8) can be used to increase the ordering in the liquid crystal elastomers from a 'native' random ordering of nematic domains to a quasi-macroscopically-ordered nematic film. Applied alternating electric fields have recently been shown to affect stem cell differentiation[23] (depending on the frequency of the applied field). This offers the possibility to affect both, the ordering within the scaffold that affects stem cell differentiation in addition to the effect of the applied ac field.

Anisotropic liquid crystal elastomer films are also prepared by performing the cross-linking reaction inside liquid crystal cells with unidirectionally rubbed alignment layers to achieve nematic phase homogeneous (planar) alignment during cross-linking and cooling.[24]

Figure 11:
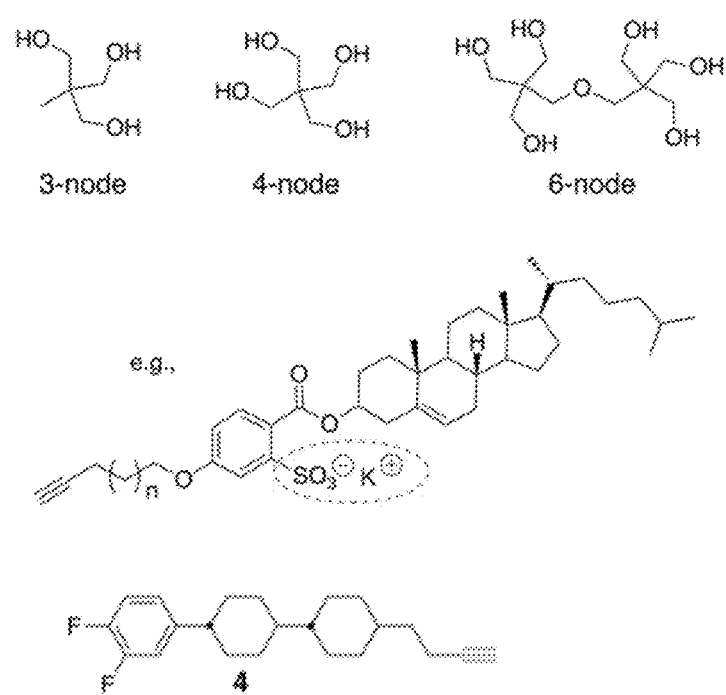
FIG. 11 relates to alternative structural motifs to tune the properties (porosity, degradation rate) of the elastomer: increasing the number of nodes in the SBC should enhance stiffness and mechanical strengths.
Figure 12:
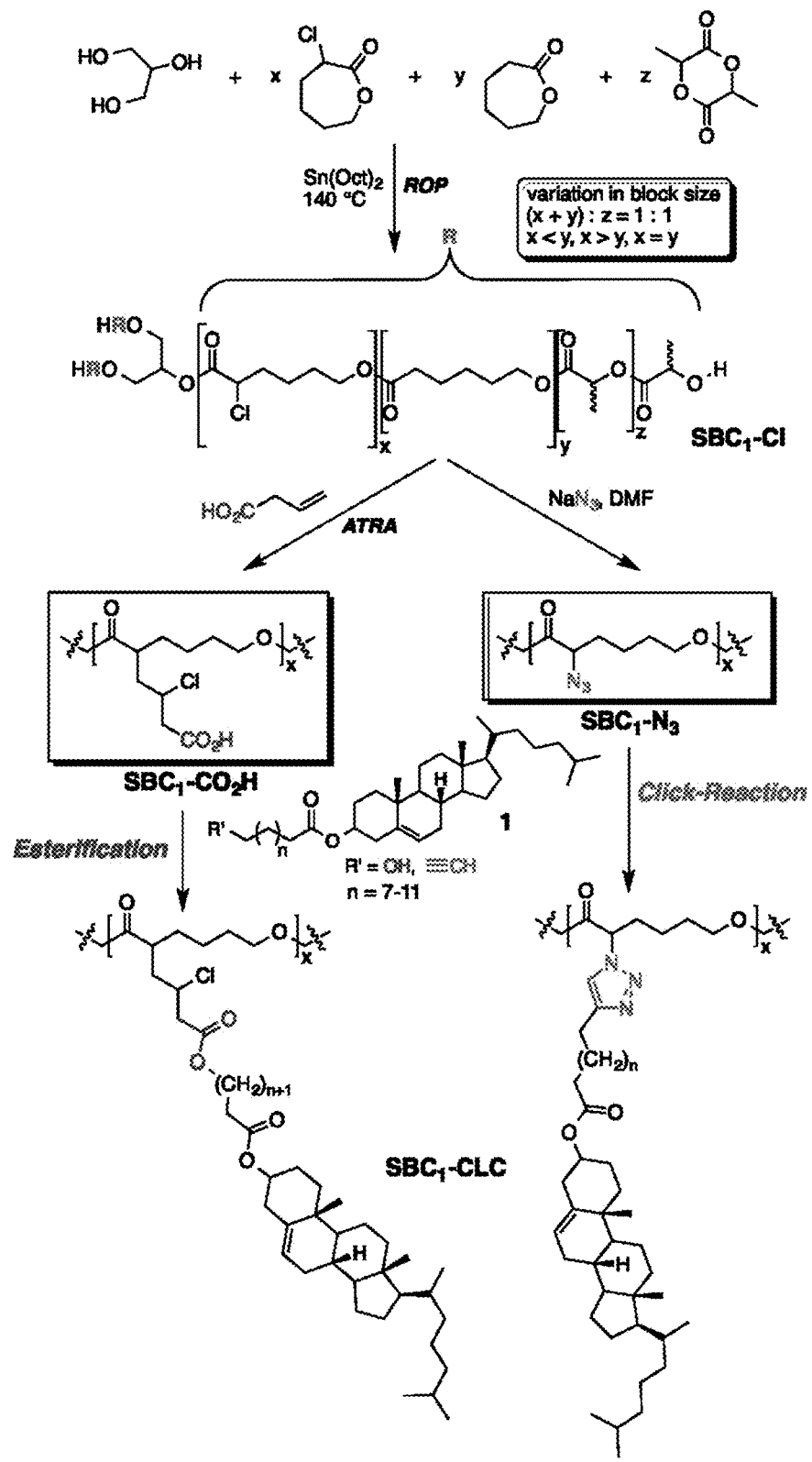
FIG. 12 relates to synthetic pathway to star block copolymers (SBCs) used for the preparation of SRS materials with biocompatible cholesterol liquid crystal pendants (ROP-ring opening polymerization, ATRA-atom transfer radical addition).

Additional possibilities arise from the chemical modification of either the core structure of the SBC (the node) or the structure of the liquid crystal pendants (FIG. 11). The first option can be achieved by selecting other central nodes with a higher branching number that will enhance the mechanical strengths and stiffness of the SRS substrates due to the increase in branching points. The latter option is most conveniently realized by replacing the cholesterol moiety for another biocompatible LC that will increase the hydrophilicity of the final material.

In summary, the versatility of the synthetic approach and a toolbox of building blocks for scaffold elastomers create highly modular materials for 4D cell culture studies (3D plus time) and allows for a wide array of cell types to be used. These elastomers have been tested as implantable scaffolds and injectable carriers with tunable degradation rate in the past, which permits fast translation of the research results from the 4D cell culture tested in the laboratory to cell based therapeutic strategies.

The on-demand differentiation of stem cells using external stimuli ensures extracellular matrix formation and enhanced biomechanical properties of the cells for successful transplantation of the cell-elastomer construct. As a short-term target, we envision into pilot studies, where the dynamics of tissue regeneration during patch elastomer biodegradation (as a bioresorbable component) will be investigated. Such studies provide important insights into the biomechanic differences between externally stimulated, differentiated cell-elastomer constructs versus 'standard' induced differentiated cell-elastomer constructs (i.e. addition of typical components for differentiation to adipogenic cell lines such as insuline, dexamethasone and IBMX). For drug delivery systems, our elastomers could be made to hold a desirable drug load. Modifying the pore size, which allows long-term drug storage, controlled, slow release, and molecular stability can achieve this. The preparation of the elastomers can be quickly modified to obtain patches (lamellar systems) where the liquid crystalline phase behavior will have an effect on drug release control. These elastomers can be engineered into a wide variety of sizes, compositions, surface morphologies, and sustained release of encapsulated drugs or therapeutic treatments.

The following articles are hereby fully incorporated by reference.

[1] E. Fuchs and J. A. Segre, Stem cells: A new lease on life, Cell 100(1), 143-155 (2000).

[2] X. H. Liu, X. B. Jin, and P. X. Ma, Nanofibrous hollow microspheres self-assembled from star-shaped polymers as injectable cell carriers for knee repair, Nat. Mater. 10, 398-406 (2011).

[3] S. M. Willerth and S. E. Sakiyama-Elbert, Combining stem cells and biomaterial scaffolds for constructing tissues and cell delivery, StemBook, Ed. The Stem Cell Research Community, StemBook, doi/10.3824/stembook.1.1.1 (2008).

[4] (a) N. Jaiswal, S. E. Haynesworth, A. I. Caplan, and S. P. Bruder, Osteogenic differentiation of purified culture-expanded human mesenchymal stem cells in vitro, J. Cell. Biochem. 64, 295-312 (1997); (b) L. C. Amado, A. P. Saliaris, K. H. Schuleri, M. St John, J. S. Xie, S. Cattaneo, D. J. Durand, K. Fitton, J. Q. Kuang, G. Stewart, S. Lehrke, W. W. Baumgartner, B. J. Martin, A. W. Heldman, and J. M. Hare, Cardiac repair with intramyocardal injection of allogeneic mesenchymal stem cells after myocardial infarction, Proc. Natl. Acad. Sci. U.S.A. 102, 11474-11479 (2005).

[5] Y. Hong, Y. Gong, C. Gao, and J. Shen, Collagen-coated polylactide microcarriers/chitosan hydrgel composite: Injectable scaffold for cartilage regeneration J. Biomed. Mater. Res., Part A 85, 628-637 (2008).

[6] (a) S. Choi, Y. Zhang, Y. Yeh, A. L. Wooten, and Y. Xia, Biodegradable porous beads and their potential applications in regenerative medicine, J. Mater. Chem. 22, 11442-11451 (2012); (b) Y. Senuma, S. Franceschin, J. G. Hilborn, P. Tissières, I. Bisson, and P. Frey, Bioresorbable microspheres by spinning disk atomization as injectable cell carrier: from preparation to in vitro evaluation, Biomaterials 21, 1135-1144 (2000); (c) H. J. Chung, I. K. Kim, T. G. Kim, and T. G. Park, Highly open porous biodegradable microcarriers: in vitro cultivation of chondrocytes for injectable delivery, Tissue Eng. A. 14, 607-615 (2008).

[7] C. Perka, O. Schultz, R.-S. Spitzer, K. Lindenhayn, G.-R. Burmester, and M. Sittinger, Segmental bone repair by tissue-negineered periosteal cell transplants with bioresorbable fleece and fibrin scaffolds in rabbits, Biomaterials 21, 1145-1153 (2000).

[8] E. Hany, M. A. Shaker, and H. M. Younes, Soft biodegradable elastomers based on poly(octanediol-tartarate)

for drug delivery and tissue engineering: synthesis, characterization and biocompatibility studies, Soft Mater. 9(4), 409-428 (2011).

[9] (a) M. P. Hiljanen-Vainio, P. A. Orava, and J. V. Seppala, Properties of epsilon-caprolactone/DL-lactide (epsilon-CL/DL-LA) copolymers with a minor epsilon-CL content. J. Biomed. Mater. Res. 34, 39-46 (1997); (b) A. J. Nijenhuis, D. W. Grijpma, and A. J. Pennings, Cross-linked poly(L-lactide) and poly(epsilon-caprolactone), Polymer 37, 2783-2791 (1996).

[10] H. M. Younes, E. Bravo-Grimaldo, and B. G. Amsden, Synthesis, characterization and in vitro degradation of a biodegradable elastomer, Biomaterials 25, 5261-5269 (2004).

[11] R. F. Storey, S. C. Warren, C. J. Allison, and A. D. Puckett, Methacrylate-encapped poly(d,l-lactide-co-trimethylene carbonate) oligomers. Network formation by thermal free-radical curing, Polymer 38, 6295-6301 (1997).

[12] M. Lang, R. P. Wong, and C. C. Chu, Synthesis and structural analysis of functionalized poly(-caprolactone)-based three-arm star polymers, J. Polym. Sci. Part A: Polym. Chem. 40, 1127-1141 (2002).

[13] B. NOttelet, C. Di Tommaso, K. Mondon, R., Gurny, and M. Möller, Fully biodegradable polymeric micelles based on hydrophobic- and hydrophilic-functionalized poly(lactide) block copolymers, J. Polym. Sci. Part A: Polym. Chem. 48, 3244-3254 (2010).

[14] (a) N. A. Lockwood, J. C. Mohr, L. Ji, C. J. Murphy, S. R. Palecek, J. J. de Pablo, and N. L. Abbott, Thermotropic liquid crystals as substrates for imaging the reorganization of matrigel by human embryonic stem cells, Adv. Funct. Mater. 16, 618-624 (2006); (b) A. M. Lowe, N. L. Abbott, Liquid crystalline materials for biological applications, Chem. Mater. 24, 746-758 (2012).

[15] R. Riva, L. Chafaqi, R. Jerome, and P. Lecomte, Synthesis of new substituted lactones by "click" chemistry, Archivoc 292-306 (2007).

[16] H. C. Kolb, M. G. Finn, and K. B. Sharpless, Click chemistry: diverse chemical function from a few good reactions, Angew. Chem. Int. Ed. 40, 2004-2021 (2001).

[17] H. Nandivada, L. G. Villa-Diaz, K. S. O'Shea, G. D. Smith, P. N. Krebsbach, and J. Lahann, Fabrication of synthetic polymer coatings and their use in feeder-free culture of human embryonic stem cells, Nat. Protoc. 6, 1037-1043 (2011).

[18] M. A. Matos and M. T. Cicerone, Alternating electric field affects on neural stem cell viability and differentiation, Biotechnol. Prog. 26(3), 664-670 (2010).

[19] D. L. Thomson III, P. Keller, J. Naciri, R. Pink, H. Jeon, D. Shenoy, and B. R. Ratna, Liquid crystal elastomers with mechanical properties of a muscle, Macromolecules 34, 5868-5875 (2001).

[20] R. Riva, L. Chafaqi, R. Jerome, and P. Lecomte, Synthesis of new substituted lactones by "click" chemistry, Archivoc 292-306 (2007).

[21] C. F. Soon, M. Youseffi, N. Blagden, R. Berends, S. B. Lobo, F. A. Javid, and M. Denyer, Characterization and biocompatibility study of nematic and cholesteryl liquid crystals, Proc. World Congress Engineering, Vol. II., ISBN:978-988-18210-1-0 (2009).

[22] (a) N. A. Lockwood, J. C. Mohr, L. Ji, C. J. Murphy, S. R. Palecek, J. J. de Pablo, and N. L. Abbott, Thermotropic liquid crystals as substrates for imaging the reorganization of matrigel by human embryonic stem cells, Adv. Funct. Mater. 16, 618-624 (2006); (b) A. M. Lowe, N. L. Abbott, Liquid crystalline materials for biological applications, Chem. Mater. 24, 746-758 (2012).

[23] N. A. Lockwood, M. V. Meli, A. Surjosantoso, E. B. Kim, J. J. de Pablo, and N. L. Abbott, Characterization of the interactions between synthetic LCs and model cell membranes, Liq. Cryst. 34, 1387-1396 (2007).

[24] H. C. Kolb, M. G. Finn, and K. B. Sharpless, Click chemistry: diverse chemical function from a few good reactions, Angew. Chem. Int. Ed. 40, 2004-2021 (2001).

[25] K. V. Axenov and S. Laschat, Thermotropic ionic liquid crystals, Materials 4, 206-259 (2011).

While in accordance with the Patent Statutes, the best mode and preferred embodiments have been set forth, the scope of the invention is not limited thereto, but rather by the scope of the attached claims.

What is claimed is:

1. A star block copolymer having pendant liquid crystal side chains, comprising:
   a core derived from a polyol; and
   a plurality of random block polymers comprising:
   a polymer block derived from halide substituted lactone monomers;
   a polymer block derived from lactone monomers or isomers thereof; and
   a polymer block derived from lactide monomers;
   said halide containing block polymer having a plurality of non-toxic, biocompatible liquid crystal chains pendant therefrom that are substituted for or added at said halide site; and wherein said star block copolymer is cross-linked by a crosslinking agent to form a thermoset elastomer.

2. The star block copolymer of claim 1, wherein the porosity of said copolymer is from about 5 microns to about 700 microns in the dry state; wherein said polyol core is derived from a polyol having from 2 to 8 hydroxy groups; wherein said substituted halide is a chlorine atom or a bromine atom; and wherein said crosslinking agent is a compound that is biocompatible and biodegradable with said star block copolymer.

3. The star block copolymer of claim 2, wherein said polyol core has from 3 to 8 hydroxyl groups; wherein said liquid crystal is a cholesterol-based chiral nematic liquid crystal or derivative thereof, a cholesteryl liquid crystal or a derivative thereof, or a 3,4-difluoropentyl-bicyclohexyl-base nematic liquid crystal or a derivative thereof; wherein said polyol comprises glycerol, pentaerythritol, or dipentaerythritol; wherein said lactone is ε-caprolactone, α-caprolactone, β-caprolactone, γ-caprolactone, or δ-caprolactone; wherein said lactide is D-Lactide, L-Lactide, or D,L-Lactide; and wherein said crosslinking agent is 2,2-Bis(1-caprolactone-4-yl) propane (BCP) and derivatives thereof, or Bis-caprolactone with oligoethylene glycol spacer and derivatives thereof.

4. The star block copolymer of claim 2, wherein "x" is the number of mass moles of said halide substituted lactone of said substituted lactone, wherein "y" is the number of mass moles of said lactone, and wherein "z" is the number of mass moles of said lactide, wherein "x" is from about 0.1 to about 99% based upon the total mass moles of said "x" and said "y"; wherein "x+y" is from about 1 to about 90% based upon the total mass moles of said "x", said "y", and said "z" mass moles; and wherein the amount of said core polyol is from about 0.001 to about 50 mass moles based upon the total of said "x", said "y", and said "z" mass moles.

5. The star block copolymer of claim 3, wherein "x" is the number of mass moles of said halide substituted lactone of said substituted lactone, wherein "y" is the number of mass moles of said lactone, and wherein "z" is the number of mass moles of said lactide, wherein "x" is from about 40% to about 60% based upon the total mass moles of said "x" and said "y"; wherein "x+y" is from about 5% to about 40% based upon the total mass moles of said "x", said "y", and said "z" mass moles; wherein the amount of said core polyol is from about 0.1 to about 30 mass moles based upon the total of said "x", said "y", and said "z" mass moles; and wherein said crosslinking agent is 2,2-Bis(1-caprolactone-4-yl) propane (BCP).

6. The star block copolymer of claim 3, wherein said halide substituted lactone monomer is α-chloro-ε-caprolactone or γ-bromo-ε-caprolactone, wherein said lactone monomer is ε-polycaprolactone, and wherein said lactide is D,L-lactide; and wherein said liquid crystal is cholesteryl-5 hexynoate.

7. The star block copolymer of claim 1, wherein the porosity of said star block copolymer is from about 5 microns to about 700 microns.

8. The star block copolymer of claim 2, wherein the porosity of said star block copolymer is from about 10 microns to about 500 microns.

9. The star block copolymer of claim 1, wherein the porosity of said star block copolymer is from about 10 microns to about 350 microns.

10. The star block copolymer of claim 2, wherein "x" is the number of mass moles of said halide substituted lactone, wherein "y" is the number of mass moles of said lactone, and wherein "z" is the number of mass moles of said lactide, wherein "x" is from about 5 to about 70% based upon the total mass moles of said "x" and said "y"; wherein "x+y" is from about 2 to about 80% based upon the total mass moles of said "x", said "y", and said "z" mass moles; and wherein the amount of said core polyol is from about 0.01 to about 40 mass moles based upon the total of said "x", said "y", and said "z" mass moles.

11. A smart responsive scaffold comprising the composition of claim 1.

12. A smart responsive scaffold comprising the composition of claim 2.

13. A smart responsive scaffold comprising the composition of claim 3.

14. A smart responsive scaffold comprising the composition of claim 4.

15. A smart responsive scaffold comprising the composition of claim 5.

16. A smart responsive scaffold comprising the composition of claim 6.

17. A smart responsive scaffold comprising the composition of claim 7.

18. A smart responsive scaffold comprising the composition of claim 8.

19. A smart responsive scaffold comprising the composition of claim 9.

20. A smart responsive scaffold comprising the composition of claim 10.

* * * * *